United States Patent [19]

Nakaguchi et al.

[11] Patent Number: 4,725,608
[45] Date of Patent: Feb. 16, 1988

[54] SEMICARBAZIDE DERIVATIVES, PROCESSES FOR PREPARATION THEREOF AND PHARMACEUTICAL COMPOSITION COMPRISING THE SAME

[75] Inventors: Osamu Nakaguchi; Norihiko Shimazaki, both of Toyonaka; Yoshio Kawai, Tokyo; Masashi Hashimoto, Takarazuka; Michie Nakatuka, Yokohama, all of Japan

[73] Assignee: Fujisawa Pharmaceutical Co., Ltd., Osaka, Japan

[21] Appl. No.: 673,845

[22] Filed: Nov. 21, 1984

[30] Foreign Application Priority Data

Nov. 21, 1983 [GB] United Kingdom ................ 8330978
Jul. 9, 1984 [GB] United Kingdom ................ 8417453

[51] Int. Cl.$^4$ ................ A61K 31/435; C07D 211/98
[52] U.S. Cl. ................ 514/353; 546/306; 564/18; 564/34; 564/37; 544/164; 544/224; 548/958
[58] Field of Search ................ 546/306; 514/353

[56] References Cited

U.S. PATENT DOCUMENTS

| | | | |
|---|---|---|---|
| 3,285,957 | 11/1966 | Baker et al. | 564/34 |
| 3,318,680 | 5/1967 | Levitt | 564/18 X |
| 3,511,875 | 5/1970 | Brantley | 560/136 |
| 4,013,669 | 3/1977 | Parsons | 546/309 |
| 4,088,653 | 5/1978 | Knaus et al. | |

FOREIGN PATENT DOCUMENTS

| | | |
|---|---|---|
| 2801187 | 7/1978 | Fed. Rep. of Germany . |
| 1521959 | 4/1968 | France . |
| 480309 | 12/1969 | Switzerland . |
| 480308 | 12/1969 | Switzerland . |
| 1377397 | 12/1974 | United Kingdom . |
| 1382974 | 2/1975 | United Kingdom . |
| 2058762 | 4/1981 | United Kingdom . |

OTHER PUBLICATIONS

Koelzer, et al., Chem. Abstracts, vol. 53 (1959) entry 22506g.
Nathanson, et al., Chem. Abstracts, vol. 78 (1973) entry 16053w.
Podgornoya, et al., Chem. Abstracts, vol. 61 (1964) entry 14634a.
Zinner, et al., Chem. Abstracts, vol. 64 (1966) entry 17531e.
Chemical Abstracts, vol. 71, 3166k.
Nam et al, Journal of the Chemical Society, 1956, 2160–2165.
Journal of Pharmaceutical Sciences, vol. 72, No. 10, Oct. 1983, pp. 1213–1215, Kornet et al: Synthesis and Anticonvulsant Testing of 4-phenylsemicarbazides.
Journal of Medicinal Chemistry, 1968, pp. 171–172, Wilcox: Synthesis and herbicidal activity of 1,1-dimethy-land 2-methyl-4-phenylsemicarbazides.
Wilcox, Journal of the Medicinal Chemistry, vol. 11, 171–172 (1968).
Knaus et al, Journal of the Medicinal Chemistry, vol. 25, 720–723 (1982).
Chemical Abstracts, vol. 67, 108582p.
Journal of Pharmaceutical Sciences, vol. 72, No. 10, Oct. 1983, pp. 1213–1215, Kornet et al: Synthesis and Anticonvulsant Testing of 4-phenylsemicarbazides.

*Primary Examiner*—Donald G. Daus
*Assistant Examiner*—William A. Teoli, Jr.
*Attorney, Agent, or Firm*—Oblon, Fisher, Spivak, McClelland & Maier

[57] ABSTRACT

New semicarbazide derivatives of the formula:

$$\begin{array}{c} R^2 \quad R^1 \quad R^5 \\ \diagdown \quad | \quad | \\ N-N-C-N-R^4 \\ \diagup \quad \quad \| \\ R^3 \quad \quad X \end{array}$$

wherein
  $R^1$ is hydrogen,
  $R^2$ is hydrogen, lower alkyl, ar(lower)alkyl, lower alkenyl or aryl,
  $R^3$ is lower alkyl, ar(lower)alkyl, lower alkenyl or aryl, or
  $R^2$ and $R^3$ are taken together to form ($C_2$–$C_6$)alkylidene group optionally substituted with aryl or taken together with the adjacent nitrogen atom to form a saturated or unsaturated, 5- or 6-membered heterocyclic group optionally substituted with aryl; or
  $R^1$ and $R^2$ are taken together with the adjacent nitrogen atoms to form a saturated or unsaturated, 5- or 6-membered heterocyclic group or 1,2-diazaspiroalkane-1,2-diyl group,
  $R^3$ is hydrogen, lower alkyl, ar(lower)alkyl, lower alkenyl or aryl;
  $R^4$ is aryl which may have substituent(s) selected from lower alkyl, halogen, lower alkoxy, lower alkylamino, halo(lower)alkyl, hydroxy, lower alkanoyl, esterified carboxy and carboxy,
  $R^5$ is hydrogen or lower alkyl, and
  X is O or S, provided that the lower alkyl group for $R^3$ is ($C_3$–$C_6$)alkyl, when $R^2$ is hydrogen or ($C_1$–$C_2$) alkyl and $R^4$ is aryl optionally having substituent(s) selected from groups consisting of halogen, lower alkyl, lower alkoxy and halo(lower)alkyl, and pharmaceutically acceptable salts thereof, and processes for preparation thereof and pharmaceutical composition comprising the same.

These derivatives and salts thereof are useful as antiinflammatory and analgesic agents.

10 Claims, No Drawings

SEMICARBAZIDE DERIVATIVES, PROCESSES FOR PREPARATION THEREOF AND PHARMACEUTICAL COMPOSITION COMPRISING THE SAME

The present invention relates to novel semicarbazide derivatives. More particularly, it relates to novel semicarbazide derivatives which have antiinflammatory and analgesic activities, to processes for preparation thereof, to pharmaceutical composition comprising the same, and to methods of using the same therapeutically in the treatment of inflammation and various pains in human being and animals.

Accordingly, one object of this invention is to provide novel semicarbazide derivatives which are useful as antiinflammatory and analgesic agents.

Another object of this invention is to provide processes for preparation of said semicarbazide derivatives.

A further object of this invention is to provide pharmaceutical composition comprising, as an active ingredient, said semicarbazide derivative.

Still further object of this invention is to provide a method of using said semicarbazide derivatives in the treatment of inflammation and various pains in human being and animals.

Some N-substituted-1,2,3,6-tetrahydropyridine derivatives having antiinflamatory and analgesic activities have been known as described, for example, in U.S. Pat. No. 4,088,653 and Journal of Medicinal Chemistry Vol. 25, 720–723, 1982.

And some semicarbazide derivatives having similar chemical structure to the object compounds of this invention have been known as described, for example, in Journal of Medicinal Chemistry Vol. 11, 171–172, 1968, Journal of Chemical Society 1956, 2160–2165 and France Patent No. 1,521,959. But it has not been known that these compounds possess antiinflammatory and analgesic activities.

The object semicarbazide derivatives are novel and can be represented by the following general formula [I]:

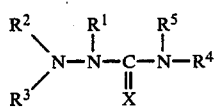

[I]

wherein $R^1$ is hydrogen,
$R^2$ is hydrogen, lower alkyl, ar(lower)alkyl, lower alkenyl or aryl,
$R^3$ is lower alkyl, ar(lower)alkyl, lower alkenyl or aryl, or
$R^2$ and $R^3$ are taken together to form $(C_2-C_6)$-alkylidene group optionally substituted with aryl or taken together with the adjacent nitrogen atom to form a saturated or unsaturated, 5- or 6-membered heterocyclic group optionally substituted with aryl; or
$R^1$ and $R^2$ are taken together with the adjacent nitrogen atoms to form a saturated or unsaturated, 5- or 6-membered heterocyclic group or 1,2-diazaspiroalkane-1,2-diyl group,
$R^3$ is hydrogen, lower alkyl, ar(lower)alkyl, lower alkenyl or aryl;
$R^4$ is aryl which may have substituent(s) selected from lower alkyl, halogen, lower alkoxy, lower alkylamino, halo(lower)alkyl, hydroxy, lower alkanoyl, esterified carboxy and carboxy,
$R^5$ is hydrogen or lower alkyl, and
X is O or S,
provided that the lower alkyl group for $R^3$ is $(C_3-C_6)$-alkyl, when $R^2$ is hydrogen or $(C_1-C_2)$alkyl and $R^4$ is aryl optionally having substituent(s) selected from groups consisting of halogen, lower alkyl, lower alkoxy and halo(lower)alkyl.

The object compound [I] and its pharmaceutically acceptable salt can be prepared by the following processes.

Process 1

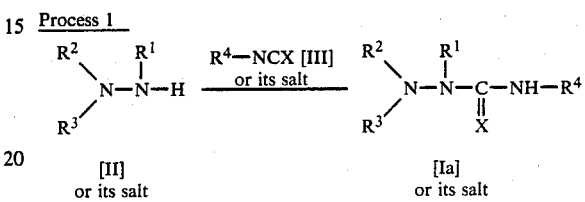

Process 2

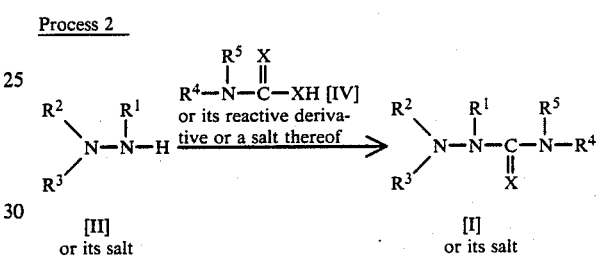

Process 3

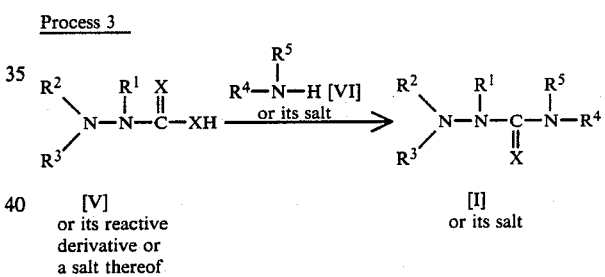

Process 4

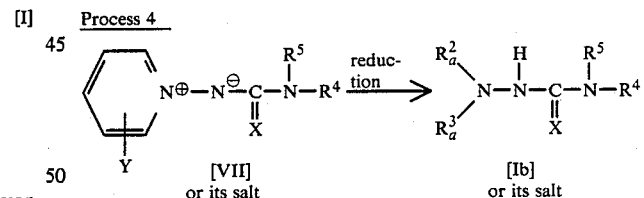

Process 5

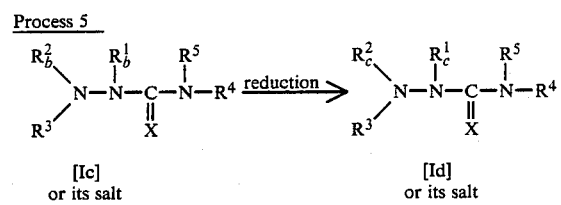

Process 6

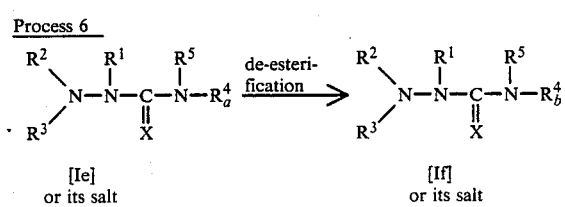

wherein $R^1$, $R^2$, $R^3$, $R^4$, $R^5$ and X are each as defined above,

Y is hydrogen or aryl, $R^2_a$ and $R^3_a$ are taken together with the adjacent nitrogen atom to form a partially or fully saturated 6-membered heterocyclic group optionally substituted with aryl, $R^1_b$ and $R^2_b$ are taken together with the adjacent nitrogen atoms to form unsaturated 5- or 6-membered heterocyclic group, $R^1_c$ and $R^2_c$ are taken together with the adjacent nitrogen atoms to form a partially or fully saturated 5- or 6-membered heterocyclic group, $R^4_a$ is aryl substituted with esterified carboxy, and $R^4_b$ is aryl substituted with carboxy, provided that the lower alkyl group for $R^3$ is $(C_3-C_6)$-alkyl, when $R^2$ is hydrogen or $(C_1-C_2)$alkyl and $R^4$ is aryl optionally having substituent(s) selected from groups consisting of halogen, lower alkyl, lower alkoxy and halo(lower)alkyl.

In the above and subsequent description of the present specification, suitable examples of the various definitions to be included within the scope of the invention are explained in detail in the following The term "lower" is intended to mean a group having 1 to 6 carbon atom(s), unless otherwise provided.

Suitable examples of lower alkyl for $R^2$, $R^3$ and $R^5$ may be a straight or branched one such as methyl, ethyl, propyl, isopropyl, butyl, isobutyl, t-butyl, pentyl, hexyl or the like.

Suitable examples of lower alkenyl for $R^2$ and $R^3$ may be vinyl, allyl, 1-propenyl, 3-butenyl, 4-pentenyl, 5-hexenyl or the like.

Suitable examples of aryl for $R^2$, $R^3$, $R^4$, Y and the substituent on the heterocyclic group formed by $R^2$ and $R^3$ or $R^2_a$ and $R^3_a$ may be phenyl, naphthyl or the like.

Suitable examples of ar(lower)alkyl for $R^2$ and $R^3$ may be benzyl, phenethyl, phenylpropyl, benzhydryl, trityl or the like.

Suitable examples of the $(C_2-C_6)$alkylidene group formed by $R^2$ and $R^3$ may be ethylidene, propylidene, isopropylidene, butylidene, pentylidene, hexylidene or the like. These $(C_2-C_6)$ alkylidene groups may be substituted with aryl group(s), wherein said aryl group(s) may have suitable substituent(s). Suitable examples of the aryl group optionally having substituent(s) may be phenyl, 2-methylphenyl, 4-chlorophenyl, naphthyl, or the like. Accordingly, suitable examples of the $(C_2-C_6)$alkylidene group having such substituent(s) may be 1-phenylethylidene, 2-phenylethylidene, 1,2-diphenylethylidene, 1-phenylpropylidene, 1-(4-chlorophenyl)ethylidene or the like.

Suitable examples of the saturated or unsaturated, 5- or 6-membered heterocyclic group formed by $R^2$, $R^3$ and the adjacent nitrogen atom may be pyrrolidin-1-yl, pyrrolin-1-yl, imidazolidin-1-yl, imidazolin-1-yl, imidazol-1-yl, pyrazolidin-1-yl, morpholino, piperidino, piperazin-1-yl, 1,4-dihydropyridin-1-yl, 1,2-dihydropyridin-1-yl, 1,2,3,6-tetrahydropyridin-1-yl or the like. These heterocyclic groups may be substituted with the aryl group as exemplified before. Suitable examples of these heterocyclic groups having the aryl group may be 4-phenyl-1,2,3,6-tetrahydropyridin-1-yl, 4-phenylpiperazin-1-yl or the like.

Suitable examples of the partially or fully saturated 6-membered heterocyclic group formed by $R^2_a$, $R^3_a$ and the adjacent nitrogen atom may be piperidino, 1,4-dihydropyridin-1-yl, 1,2-dihydropyridin-1-yl or 1,2,3,6-tetrahydropyridin-1-yl. Said heterocyclic groups may be substituted with the aryl group as exemplified for Y. Suitable examles of said heterocyclic groups having the aryl group may be 4-phenyl-1,2,3,6-tetrahydropyridine, 4-phenylpiperidino or the like.

Suitable examples of the saturated or unsaturated, 5- or 6-membered heterocyclic group formed by $R^1$, $R^2$ and the adjacent nitrogen atoms may be pyrazolidinediyl, perhydropyridazinediyl, pyrazolinediyl, 1,2,3,4-tetrahydropyridazinediyl, 1,2,3,6-tetrahydropyridazinediyl or the like.

Suitable examples of the unsaturated 5- or 6-membered heterocyclic group formed by $R^1_b$, $R^2_b$ and the adjacent nitrogen atoms may be 1,2,3,6-tetrahydropyridazinediyl, 1,2,3,4-tetrahydropyridazinediyl, 1,2-dihydropyridazinediyl, pyrazolinediyl or the like.

Suitable examples of the partially or fully saturated 5- or 6-membered heterocyclic group formed by $R^1_c$, $R^2_c$ and the adjacent nitrogen atoms may be 1,2,3,6-tetrahydropyridazinediyl, perhydropyridazinediyl, pyrazolidinediyl, or the like.

Suitable examples of the 1,2-diazaspiralkane-1,2-diyl group formed by $R^1$, $R^2$ and the adjacent nitrogen atoms may be 1,2-diazaspiro[2,5]octane-1,2-diyl, 1,2-diazaspiro[2,6]nonane-1,2-diyl, 1,2-diazaspiro[4,5]-decane-1,2-diyl or the like.

The aryl group for $R^4$ may be substituted with substituent(s) selected from the aforementioned lower alkyl; halogen [e.g. fluorine, chlorine, bromine and iodine]; lower alkoxy [e.g. methoxy, ethoxy, propoxy, butoxy, t-butoxy, pentyloxy, hexyloxy, etc.]; lower alkylamino [e.g. methylamino, ethylamino, propylamino, hexylamino, dimethylamino, diethylamino, dipropylamino, dihexylamino, etc.]; halo(lower)alkyl [e.g. chloromethyl, fluoromethyl, bromomethyl, difluoromethyl, dichloromethyl, trifluoromethyl, trichloromethyl, 2-fluoroethyl, etc.]; hydroxy; lower alkanoyl [e.g. formyl, acetyl, propionyl, butyryl, isobutyryl, pivaloyl, valeryl, hexanoyl, etc.]; esterified carboxy such as substituted or unsubstituted lower alkoxycarbonyl [e.g. methoxycarbonyl, ethoxycarbonyl, propoxycarbonyl, butoxycarbonyl, hexyloxycarbonyl, 2-iodoethoxycarbonyl, 2,2,2-trichloroethoxycarbonyl, etc.], substituted or unsubstituted aryloxycarbonyl [e.g. phenoxycarbonyl, 4-nitrophenoxycarbonyl, 2-naphtyloxycarbonyl, etc.], substituted or unsubstituted ar(lower)alkoxycarbonyl [e.g. benzyloxycarbonyl, phenethyloxycarbonyl, benzhydryloxycarbonyl, 4-nitrobenzyloxycarbonyl, etc.]; and carboxy.

Suitable examples of the aryl group for $R^4$ having such substituent(s) may be lower alkyl substituted aryl [e.g. o-tolyl, m-tolyl, p-tolyl, etc.], halogenated aryl [e.g. 2-fluorophenyl, 3-fluorophenyl, 4-fluorophenyl, 2-chlorophenyl, 3-chlorophenyl, 4-chlorophenyl, 4-bromophenyl, 4-iodophenyl, 2,4-difluorophenyl, 3,4-difluorophenyl, 4-fluoronaphthalen1-yl, etc.], lower alkoxy substituted aryl [e.g. 2-methoxyphenyl, 4-methoxyphenyl, 4-ethoxyphenyl, 4-hexyloxyphenyl, 5-methoxynaphthalen-1-yl, etc.], lower alkylamino substituted aryl [e.g. 4-methylaminophenyl, 4-dimethylaminophenyl, 4-diethylaminophenyl, 5-dimethylaminonaphthalen-1-yl, etc.], halo(lower)alkyl substituted aryl [e.g. 4-trifluoromethylphenyl, 2-trifluoromethylphenyl, 4-trichloromethylphenyl, 4-trifluoromethylnaphthalen-1-yl, etc.], hydroxy substituted aryl [e.g. 4-hydroxyphenyl, 3-hydroxyphenyl, 2-hydroxyphenyl, 2-hydroxynaphthalen-1-yl, etc.], lower alkanoyl substituted aryl [e.g. 4-formylphenyl, 4-acetylphenyl, 2-propionylphenyl, etc.], esterified carboxy substituted aryl [e.g. 4-methoxycarbonylphenyl, 2-ethoxycarbonylphenyl, 4-phenoxycarbonylphenyl, 4-benzyloxycarbonylphenyl, etc.], carboxy substituted aryl [e.g. 4-carboxyphenyl, 3-carboxyphenyl, 2-carboxyphenyl, etc.], lower alkyl and halogen substituted aryl [e.g. 4-fluoro-2-methylphenyl, 2-fluoro-4-methylphenyl, 4-fluoro-2-ethylphenyl, 2,4-difluoro-6-methylphenyl, etc.], halogen and lower alkoxy substituted aryl [e.g. 3-chloro-2-methoxyphenyl, 4-fluoro-2-methoxyphenyl, 2-fluoro-4-ethoxyphenyl, 2,4-difluoro-6-methoxyphenyl, etc.] or the like.

Suitable examples of the esterified carboxy substituted aryl for $R^4{}_a$ and the carboxy substituted aryl for $R^4{}_b$ can be referred to those exemplified for $R^4$ as mentioned above.

Suitable pharmaceutically acceptable salts of the object compounds [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamne salt, etc.], an organic acid salt [e.g. formate, acetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, aspartic acid salt, glutamic acid salt, etc.], and the like.

In this respect, it is to be noted the compounds [Ia], [Ib], [Ic], [Id], [Ie] and [If] are included within the scope of the compound [I], and accordingly the suitable salts of these compounds [Ia], [Ib], [Ic], [Id], [Ie] and [If] are to be referred to those as exemplified for the object compound [I] mentioned above.

The processes for preparing the object compounds [I] and their salts are explained in detail in the following.

Process 1

The object compound [Ia] and its salt can be prepared by reacting a compound [II] or its salt with a compound [III] or its salt.

Suitable salts of the compounds [II] and [III] may be the same as those exemplified for the compound [I].

This reaction is usually carried out in a solvent such as water, methanol, ethanol, dioxane, tetrahydrofuran, benzene, chloroform, methylene chloride or any other organic solvent which does not adversely influence the reaction.

The reaction temperature is not critical, and the reaction is usually carried out under cooling to warming.

Process 2

The object compound [I] and its salt can be prepared by reacting a compound [II] or its salt with a compound [IV] or its reactive derivative at the carboxy, dithiocarboxy, mercaptocarbonyl or hydroxy thiocarbonyl group or a salt thereof.

Suitable salts of the compound [II] may be an acid addition salt exemplified for the compound [I].

Suitable reactive derivative at the carboxy, dithiocarboxy, mercaptocarbonyl or hydroxy thiocarbonyl group of the compound [IV] may include an ester, an acid halide, an acid anhydride and the like. The suitable examples of the reactive derivatives may be an acid halide [e.g. acid chloride, acid bromide, etc.]; a symmetrical acid anhydride; a mixed acid anhydride with an acid such as aliphatic carboxylic acid [e.g. acetic acid, pivalic acid, etc.], substituted phosphoric acid [e.g. dialkylphosphoric acid, diphenylphosphoric acid, etc.]; an ester such as lower alkyl ester [e.g. methyl ester, ethyl ester, propyl ester, hexyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxy-chloro-1H-benzotriazole, or the like. These reactive derivatives can be optionally selected according to the kind of the compound [IV] to be used.

Suitable salts of the compound [IV] and its reactive derivative may be the same as those exemplified for the compound [I].

The reaction is usually carried out in a conventional solvent such as water, acetone, dioxane, chloroform, methylene chloride, ethylene chloride, tetrahydrofuran, ethyl acetate, N,N-dimethylformamide, pyridine or any other organic solvent which does not adversely influence the reaction. Among these solvents, hydrophilic solvents may be used in a mixture with water.

When the compound [IV] is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like. The reaction is also preferably carried out in the presence of a conventional base such as triethylamine, pyridine, sodium hydroxide or the like.

The reaction temperature is not critical, and the reaction can be carried out under cooling to heating.

Process 3

The object compound [I] and its salt can be prepared by reacting a compound [V] or its reactive derivative at the carboxy, dithiocarboxy, mercaptocarbonyl or hydroxy thiocarbonyl group or a salt thereof with a compound [VI] or its salt.

Suitable reactive derivatives at the carboxy, dithiocarboxy, mercaptocarbonyl or hydroxy thiocarbonyl group of the compound [V] and suitable salts of the compound [V] and its reactive derivative may be the same as those exemplified for the compound [IV] in the above Process 2.

Suitable salts of the compound [VI] may be the same as those exemplified for the compound [I].

This reaction can be carried out substantially in the same manner as Process 2, and therefore the reaction made and reaction conditions [e.g. solvent, condensing agent, reaction temperature, etc.] of this reaction are to be referred to those as explained in Process 2.

Process 4

The object compound [Ib] and its salt can be prepared by reducing a compound [VII] or its salt.

The reaction can be carried out in a conventional manner, namely, chemical reduction or catalytic reduction.

Suitable reducing agents to be used in chemical reduction are a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, borane, diborane, etc.] and the like.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reaction of this process is usually carried out in a solvent such as water, alcohol [e.g. methanol, ethanol, propanoyl, etc.], acetic acid, diethyl ether, dioxane, tetrahydrofuran, etc. or a mixture thereof.

The reaction is preferably carried out under somewhat milder conditions such as under cooling to warming.

In this process, the pyridinio moiety of the compound [VII] is reduced to piperidino, 1,4-dihydropyridin-1-yl, 1,2-dihydropyridin-1-yl or 1,2,3,6-tetrahydropyridin-1-yl group according to the reducing method and the reagent to be used in this process.

Process 5

The object compound [Id] and its salt can be prepared by reducing a compound [Ic] or its salt.

This reaction can be carried out substantially in the same manner as Process 4, and therefore the reaction mode and reaction conditions [e.g. reduction method, reducing agent, solvent, reaction temperature, etc.] of this reaction are to be referred to those as explained in Process 4.

Process 6

The object compound [If] and its salt can be prepared by subjecting a compound [Ie] or its salt to de-esterification reaction.

The reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4,3,0]-non5-ene, 1,4-diazabicyclo[2,2,2]octane, 1,8diazabicyclo[5,4,0]undec-7-ene, or the like. Suitable acid may include an organic acid [e.g. formic acid, acetic acid, propionic acid, trichloroacetic acid, trifluoroacetic acid, etc.]and an inorganic acid [e.g. hydrochloric acid, hydrobromic acid, sulfuric acid, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction may be the same catalysts as exemplified in Process 4.

The reduction is usually carried out in a conventional solvent which does not adversely influence the reaction such as water, methanol, ethanol, propanol, N,N-dimethylformamide, or a mixture thereof. Additionally, in case that the abovementioned acids to be used in chemical reduction are in liquid, they can also be used as a solvent. Further, a suitable solvent to be used in catalytic reduction may be the abovementioned solvent, and other conventional solvent such as diethyl ether, dioxane, tetrahydrofuran, etc., or a mixture thereof.

The reaction temperature of this reduction is not critical and the reaction is usually carried out under cooling to warming.

The object compounds [I] obtained by the above processes are isolated and purified by a conventional manner such as recrystallization, reprecipitation, column chromatography or the like.

Among the starting compounds [IV], [V] and [VII], new compounds can be prepared by the methods of Preparations mentioned later and any process known in the art for preparing structurally analogous compounds thereto.

It is to be noted that each of the object compound [I] and the starting compounds [II] to [VII] may include one or more stereoisomers due to asymmetric carbon atoms in the molecule, and all of such isomers of the compounds I] to [VII] are included within the scope of this invention.

The new semicarbazide derivatives [I] and pharmaceutically acceptable salt thereof possess anti-inflammatory and analgesic activities, and are useful for a therapeutic treatment of inflammation and various pains [e.g. headache, toothache, menorrhalgia, etc.].

For therapeutic purpose, the compounds according to the present invention can be used in a form of pharmaceutical preparation containing one of said compounds, as an active ingredient, in admixture with a pharmaceutically acceptable carried such as an organic or inorganic solid or liquid excipient suitable for oral or parenteral administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compounds [I] will vary depending upon the age and condition of the patient, an average single dose of about 0.1 mg, 1 mg, 10 mg, 50 mg, 100 mg, 250 mg, 500 mg and 1000 mg of the compounds [I] may be effective for treating inflammation and various pains. In general, amounts between 0.1 mg/body and about 1,000 mg/body may be administered per day.

In order to illustrate the usefulness of the object compounds [I], the pharmacological test data of the representative compound [I] are shown in the following.

[A] ANTIINFLAMMATORY ACTIVITY (1) Carrageenin foot edema (1) Test Method

Five male Sprague-Dawley rats weighing about 200 g were used per group. Paw edama was induced by subplantar injection of 1% carrageenin (0.1 ml/rat) into the right hind paw. The test drug was suspended in 0.5% methylcellulose and administered orally 60 minutes before phlogogen. Paw volume was measured with plethysmometer (Ugo Bazil Co., Ltd.) by water displacement immersing the paw to the lateral malleolus. The difference of paw volume before and 3 hours after the phlogogen was designated as edema volume. The data were analyzed statistically by student's t-test.

| (ii) Test Results: | |
|---|---|
| Test compound (Example No.) | Inhibition (%) (Dose: 32 mg/kg) |
| Example 1 | 54.7 |
| Example 7 | 78.8 |
| Example 26 | 45.0 |
| Example 27 | 39.0 |
| Example 36 | 35.5 |

(2) Arthus foot edema (i) Test Method

Five male Sprague-Dawley rate weighing about 200 g were used per group. Paw edema was induced by intravenous injection of egg albumin (0.5 mg/rat) and subplantar injection of anti egg albumin antiserum (0.1 ml/rat) in Arthus type foot edema. The test drug was suspended in methylcellulose and administered orally 60 min. before phlogogen. Paw volume was measured with plethysmometer (Ugo Bazil Co., Ltd.) by water displacement immersing the paw to the lateral malleolus. The difference of paw volume before and 3 hours after the phlogogen was designated as edema volume. The data were analyzed statistically by student's t-test.

| (ii) Test Result: | |
|---|---|
| Test Compound (Example No.) | Inhibition (%) (Dose: 100 mg/kg) |
| Example 1 | 33.3 |

[B] ANALGESIC ACTIVITY (1) Acetic acid induced writhing (i) Test Method

Ten male ddY strain mice were used per group. To estimate the frequency of writhing syndrome, the animals were observed from 3 to 13 minutes after an intraperitoneal injection of 0.2 ml/10 g of 0.6% acetic acid. The drugs were given orally 60 minutes before acetic acid. The frequency of writhing syndrome in the treated animals was compared with that in the non-treated control animals.

| (ii) Test Results: | |
|---|---|
| Test compound (Example No.) | Inhibition (%) (Dose: 32 mg/kg) |
| Example 1 | 72.3 |
| Example 7 | 78.8 |
| Example 36 | 66.7 |

As being apparent from the above test results, the object compound [I] of the present invention are useful as antiinflammatory and analgesic agents.

The following Preparations and Examples are given for the purpose of illustrating the present invention in more detail.

Preparation 1

To a solution of N-amino-1,2,3,6-tetrahydropyridine hydrochloride (1.346 g) and triethylami-ne (2.024 g) in methylene chloride (60 ml) was added a solution of phenyl chloroformate (1.566 g) in methylene chloride (40 ml) and the mixture was stirred for 4 hours at 5° C. Evaporation of the solvent gave a residue, which was extracted with ethyl acetate (150 ml). The extract was washed with water and dried over magnesium sulfate. The solvent was evaporated in vacuo to give N-(phenoxy- carbonylamino)-1,2,3,6-tetrahydropyridine (2.01 g), which was recrystallized from diisopropyl ether to give the desired compound (0.732 g) as colorless needles. mp: 124°-125.5° C.

IR (Nujol):3230, 1720, 1600, 1540 cm$^{-1}$

NMR (CDCl$_3$, δ):2.30 (2H, m), 3.06 (2H, t, J=6Hz), 3.47 (2H, m), 5.69 (2H, m), 6.33 (1H, s), 7.10–7.47 (5H, m)

Analysis: Calcd. for C$_{12}$H$_{14}$N$_2$O$_2$ Calcd.: C 66.04, H 6.47, N 12.84; Found: C 66.28, H 6.44, N 13.08.

PREPARATION 2

N-(Phenoxycarbonyl)-2-fluoroaniline (3.76 g) was obtained according to a similar manner to that of Preparation 1 from 2-fluoroaniline (2.22 g) and phenyl chloroformate (3.13 g).

IR (Nujol):3310, 1720, 1530 cm$^{-1}$

NMR (CDCl$_3$, δ):6.9-7.60 (9H, m), 8.20 (1H, br.s)

PREPARATION 3

4-(Phenoxycarbonylanino)-N,N-dimethylaniline (9.06 g) was obtained according to a similar manner to that of Preparation 1 from 4-amino-N,N-dimethylaniline (5.45 g) and phenyl chloroformate (7.52 g). mp:163.5°-164.5° C.

IR (Nujol):3340, 2940, 2855, 1720 cm$^{-1}$

PREPARATION 4

A mixture of N-aminopyridinium iodide (0.67 g), phenylisocyanate (0.39 g) and triethylamine (0.34 g) in dioxane (12 ml) was stirred for 3 hours under ice-bath cooling. The reaction mixture was diluted with water (12 ml), concentrated to a volume of ca. 5 ml, and then diluted with water. The precipitates were filtered off and the filtrate was evaporated to dryness to give N-(phenylcarbamoylimino)pyridinium ylide, which was used without further purification for the next reaction.

PREPARATION 5

To a stirred solution of N-aminopyridinium iodide (4.44 g) and triethylamine (2.02 g) in dry dioxane (60 ml) was added a solution of 4-fluorophenyl isocyanate (3.02 g) in dry dioxane (20 ml) under ice-bath cooling. After stirring for one hour, the reaction mixture was evaporated to dryness. The residue was washed with water and dried to give N-[[(4-fluorophenyl)carbamoyl]imino]pyridinium ylide (4.24 g). mp:207°–209° C.

IR (Nujol):3250, 3200, 3100, 1630, 1620 cm$^{-1}$

NMR (DMSO-d$_6$, δ):6.78–7.93 (7H, m), 8.28 (1H, s), 8.88–9.05 (2H, m)

PREPARATION 6

A mixture of N-aminopyridinium iodide (1.11 g), triethylamine (0.50 g) and 4-fluoro-N-phenoxycarbonylaniline (1.15 g) in tetrachloroethylene (40 ml) was stirred under reflux for 5 hours. After evaporation of the solvent, the residue was washed with diisopropyl ether, triturated with diethyl ether, washed with water and dried to give N-[[(4-fluoro-phenyl)carbamoyl]imino]pyridinium ylide (0.54 g).

IR (Nujol):3250, 3200, 3100, 1630, 1620, 1590 cm$^{-1}$

PREPARATION 7

N-[[(4-Fluorophenyl)carbamoyl]imino]pyridinium ylide (0.93 g) was obtained according to a similar manner to that of Preparation 6 from phenoxycarbonyliminopyridinium ylide (2.14 g) and 4-fluoroaniline (1.11 g).

IR (Nujol):3250, 3200, 3100, 1630 1620 cm$^-$

NMR (DMSO-d$_6$, δ):6.78–7.93 (7H, m), 8.28 (1H, s), 8.88–9.05 (2H, m)

EXAMPLE 1

N-Amino-1,2,3,6-tetrahydropyridine hydrochloride (3.42 g) was dissolved in a mixture of dioxane (30 ml) and water (20 ml). The solution was adjusted to pH 7.5 with 1N-aqueous sodium hydroxide and to the resultant mixture was added a solution of 4-fluorophenylisocyanate (0.548 g) in dioxane (5 ml). Then, the mixture was kept to pH 7.5 and stirred for 2 hours at 5° C. After evaporation of organic solvent, the crystalline product was collected by filtration and recrystallized from diisopropyl ether to give white needles of N-[[(4-fluorophenyl)carbamoyl]amino]-1,2,3,6-tetrahydropyridine (0.73 g). mp: 156°–157° C.

Mass:m/e=235 (M$^{30}$)

IR (Nujol):3380, 3190, 3100, 1680, 1660 cm$^{-1}$

NMR (CDCl$_3$, δ):2.31 (2H, m), 2.92 (2H, t, J=7 Hz), 5.78 (2H, m), 6.87–7.48 (4H, m)

Analysis: Calcd. for C$_{12}$H$_{14}$FN$_3$O Calcd.: C 61.26, H 6.00, N 17.84; Found: C 61.37, H 6.06, N 18.04.

EXAMPLE 2

N-[[(4-Fluorophenyl)carbamoyl]amino]-4-phenyl-1,2,3,6-tetrahydropyridine (1.07 g) was obtained according to a similar manner to that of Example 1 from N-amino-4-phenyl-1,2,3,6-tetrahydropyridine hydrochloride (1.16 g) and 4-fluorophenylisocyanate (0.91 g). mp:200.5°–212° C.

Mass:m/e=311 (M$^{30}$)

IR (Nujol):3340, 3160, 3070, 1670, 1540 cm$^{31\ 1}$

NMR (DMSO-d$_6$, δ):2.5–3.2 (4H, m), 3.3–3.7 (2H, m), 6.0–6.3 (1H, m), 6.9–7.8 (10H, m), 8.63 (1H, s)

Analysis: Calcd. for C$_{18}$H$_{18}$FN$_3$O Calcd.: C 69.44, H 5.83, N 13.50; Found: C 69.43, H 5.90, N 13.49.

EXAMPLE 3

1,1-Diisopropyl-4-(4-fluorophenyl)semicarbazide (0.38 g) was obtained according to a similar manner to that of Example 1 from 1,1-diisopropylhydrazine hydrochloride (1.50 g) and 4-fluorophenylisocyanate (1.65 g). mp : 126.5°–128° C.

Mass:m/e=253 (M+)

IR (Nujol):3320, 3080, 1680, 1500–1540 cm$^{-1}$

NMR (CDCl$_3$, δ) : 1.03 (6H, d, J=6Hz), 1.13 (6H, d, J=6Hz), 2.9–3.4 (2H , m), 5.65 (1H, br.s), 6.8–7.6 (4H, m), 8.00 (1H, br.s)

Analysis:Calcd. for C$_{13}$H$_{20}$FN$_3$O Calcd.:C 61.64, H 7.96, N 16.59; Found:C 61.44, H 7.86, N 16.43.

EXAMPLE 4

1-Benzyl-4-(4-fluorophenyl)semicarbazide (1.55 g) was obtained according to a similar manner to that of Example 1 from benzylhydrazine dihydrochloride (1.95 g) and 4-fluorophenylisocyanate (1.33 g). mp : 102° C.

IR (Nujol):3260, 1640 cm$^{-1}$

NMR (CDCl$_3$, δ):3.57 (2H, s), 4.75 (2H, s), 7.00 (2H, dd, J=6,6Hz), 7.35 (5H, s), 7.49 (2H, m), 8.66 (1H, s)

Analysis:Calcd. for C$_{14}$H$_{14}$FN$_3$O Calcd.:C 64.85, H 5.44, N 16. 21; Found:C 64.53, H 5.70, N 15.91.

EXAMPLE 5

1,1-Dially-4-(4-fluorophenyl)semicarbazide (1.16 g) was obtained according to a similar manner to that of Example 1 from 1,1-diallylhydrazine hydrochloride (1.85 g) and 4-fluorophenylisocyanate (1.37 g).

Mass:m/e=250 (M+1) IR (Film):3350, 3225, 3080, 1685 cm$^{-1}$

NMR (CDCl$_3$, δ):3.38 (4H, d, J=6Hz), 5.10–5.40 (4H, m), 5.80–6.30 (3H, m), 6.85–7.40 (4H, m), 8.00 (1H, s)

EXAMPLE 6

1,1-Diphenyl-4-(4-fluorophenyl) semicarbazide (1.88 g) was obtained according to a similar manner to that of Example 1 from 1,1-diphenylhydrazine (1.84 g) and 4-fluorophenylisocyanate (1.65 g). mp: 214°–214.5° C.

Mass:m/e=321 (M+)

IR (Nujol):3280, 1640, 1600, 1585 cm$^{-1}$

NMR (DMSO-d$_6$, δ):6.92–7.68 (14H, m), 8.93 (1H, s), 9.01 (1H, s)

Analysis: Calcd. for C$_{19}$H$_{16}$FN$_3$O Calcd.: C 71.02, H 5.02, N 13.08; Found: C 70.85, H 5.35, M 12.89.

EXAMPLE 7

To a solution of N-amino-1,2,3,6-tetrahydropyridine hydrochloride (1.346 g) and triethylamine (1.012 g) in dry methylene chloride (40 ml) was added a solution of 3-fluorophenyl isocyanate (1.37 g) in dry methylene chloride under ice-bath cooling. After stirring for one hour, the reaction mixture was evaporated to dryness. The residue was extracted with ethyl acetate (100 ml). The extract was washed with water, evaporated to dryness and recrystallized from ethyl acetate to give N-[[(3-fluorophenyl)carbamoyl]amino]-1,2,3,6-tetrahydropyridine (1.43 g). mp: 136.5°–138.5° C.

IR (Nujol):3280, 3200, 3100, 1685 cm$^{-1}$

NMR (CDCl$_3$,δ):2.33 (2H, m), 2.98 (2H, m), 3.37 (2H, m), 5.71 (2H, m), 6.37 (1H, s), 6.57-7.60 (4H, m), 8.28 (1H, s)

Analysis: Calcd. for C$_{12}$H$_{14}$FN$_3$O Calcd.: C 61.26, H 6.00, N 17.86; Found: C 61.44, H 5.83, N 17.91.

EXAMPLE 8

N-[[(4-Chlorophenyl)carbamoyl]amino]-1,2,3,6-tetrahydropyridine (1.32 g) was obtained according to a similar manner to that of Example 7 from N-amino-1,2,3,6-tetrahydropyridine hydrochloride (1.346 g) and 4-chlorophenyl isocyanate (1.536 g).

mp: 165.5°-167.5° C.

IR (Nujol):3330, 3170, 3100, 1685 cm$^{-1}$

NMR (CDCl$_3$, δ):2.35 (2H, m), 2.98 (2H, m), 3.37 (2H, m), 5.73 (2H, m), 6.25 (1H, s), 7.22 (2H, d, J=8Hz), 7.48 (2H, d, J=8Hz), 8.23 (1H, s)

Analysis: Calcd. for C$_{12}$H$_{14}$ClN$_3$O Calcd.: C 57.26, H 5.61, N 16.69; Found: C 57.15, H 5.87, N 16.78.

EXAMPLE 9

N-[[(3-Chlorophenyl)carbamoyl]amino]-1,2,3,6-tetrahydropyridine (1.52 g) was obtained according to a similar manner to that of Example 7 from N-amino-1,2,3,6-tetrahydropyridine hydrochloride (1.346 g) and 3-chlorophenyl isocyanate (1.536 g). mp: 145.5°-147° C.

IR (Nujol):3340, 3190, 3090, 1680 cm$^{-1}$

NMR (CDCl$_3$, δ):2.38 (2H, m), 3.02 (2H, m), 3.40 (2H, m), 5.73 (2H, m), 6.48 (1H, s), 6.93-7.30 (4H, m), 8.45 (1H, s)

Analysis: Calcd. for C$_{12}$H$_{14}$ClN$_3$O Calcd.: C57.26, H 5.61, N16.69; Found: C 57.39, H 5.75, N 16.67.

EXAMPLE 10

N-[[(2-Methoxy-5-chlorophenyl)carbamoyl]amino]-1,2,3,6-tetrahydropyridine (1.33 g) was obtained according to a similar manner to that of Example 7 from N-amino-1,2,3,6-tetrahydropyridine hydrochloride (1.346 g) and 2-methoxy-5-chlorophenyl isocyanate (1.842 g).

mp: 153.5°-154.5° C.

IR (Nujol):3375, 3300, 3200, 3100, 1680 cm$^{-1}$

NMR (CDCl$_3$, δ):2.35 (2H, m), 2.98 (2H, m), 3.37 (2H, m), 383 (3H, s), 5.73 (2H, m), 5.98 (1H, s), 6.65-7.27 (2H, m), 8.3 (1H, d, J=3Hz), 8.78 (1H, s)

Analysis: Calcd. for C$_{13}$H$_{16}$ClN$_3$O Calcd.: C 55.42, H 5.72, N 14.91; Found: C 55.21, H 5.74, N 14.81.

EXAMPLE 11

N-[[(4-Methoxyphenyl)carbamoyl]amino]-1,2,3,6-tetrahydropyridine (1.25 g) was obtained according to a similar manner to that of Example 7 from N-amino-1,2,3,6-tetrahydropyridine hydrochloride (1.346 g) and 4-methoxypenyl isocyanate (1.49 g).

mp: 146°-147° C.

IR (Nujol):3300, 3200, 3180, 3100, 1680 cm$^{-1}$

NMR (CDCl$_3$δ):2.33 (2H, m), 2.98 (2H, m), 3.37 (2H, m), 3.95 (3H, s), 5.73 (2H, m), 5.93 (1H, s), 6.83 (2H, d, J=8Hz), 7.83 (2H, d, J=8Hz), 8.06 (1H, s)

Analysis: Calcd. for C$_{13}$H$_{17}$N$_3$O$_2$ Calcd.: C 63.06, H 6.72, N 17.10. Found: C 63.14, H 6.93, N 16.99;

EXAMPLE 12

N-[[(2-Methoxyphenyl)carbamoyl]amino]-1,2,3,6-tetrahydropyridine (1.25 g) was obtained according to a similar manner to that of Example 7 from N-amino-1,2,3,6-tetrahydropyridine hydrochloride (1.346 g) and 2-methoxyphenyl isocyanate (1.491 g).

mp: 137°-139° C.

IR (Nujol):3330, 3200, 3100, 1680 cm$^{-1}$

NMR (CDCl$_3$, δ):2.33 (2H, m), 2.97 (2H, m), 3.37 (2H, m), 3.83 (3H,s), 5.70 (2H, m), 6.02 (1H, s), 6.87 (3H, m), 8.22 (1H, m), 8.75 (1H, s)

Analysis: Calcd. for C$_{13}$H$_{17}$N$_3$O$_2$ Calcd.: C 63.14, H 6.93, N 16.99; Found: C 63.25, H 6.91, N 16.99.

EXAMPLE 13

N-[(p-Tolylcarbamoyl)amino]-1,2,3,6-tetrahydropyridine (1.73 g) was obtained according to a similar manner to that of Example 7 from N-amino-1,2,3,6-tetrahydropyridine hydrochloride (1.346 g) and 4-methylphenyl isocyanate (1.323 g).

mp: 179°-180 ° C.

IR (Nujol):3350, 3170, 3050, 1675 cm$^{-1}$

NMR (CDCl$_3$, δ):2.28 (3H, s), 2.28 (2H, m), 2.63 (2H, t, J=7Hz), 3.35 (2H, m), 5.70 (2H, m), 5.95 (1H, s), 7.07 (2H, d, J=8Hz), 7.37 (2H, d, J=8Hz), 8.08 (1H, s)

Analysis: Calcd. for C$_{13}$H$_{17}$N$_3$O Calcd.: C 67.51, H 7.41, N 18.17; Found: C 67.85, H 7.58, N 18.12.

EXAMPLE 14

N-[[(4-Trifluoromethylpenyl)carbamoyl]amino]-1,2,3,6-tetrahydropyridine (1.9 g) was obtained according to a similar manner to that of Example 7 from N-amino-1,2,3,4-tetrahydropyridine hydrochloride (1.346 g) and 4-trifluoromethylphenyl isocyanate (1.871 g).

mp: 159.5°-161° C.

IR (Nujol):3340, 3200, 3100, 1690 cm$^{-1}$

NMR (CDCl$_3$, δ): 2.33 (2H, m), 2.97 (2H, t, J=7Hz), 3.37 (2H, m), 5.70 (2H, m), 6.25 (1H, s), 7.40-7.72 (4H, m), 8.20 (1H, s)

Analysis: Calcd. for C$_{13}$H$_{14}$F$_3$N$_3$O

Calcd.: C 54.74, H 4.95, N 14.73;

Found: C 55.18, H 5.05, N 14.79.

EXAMPLE 15

N-[(1-Naphthylcarbamoyl)amino]-1,2,3,6-tetrahydropyridine (1.63 g) was obtained according to a similar manner to that of Example 7 from N-amino-1,2,3,6-tetrahydropyridine hydrochloride (1.346 g) and 1-naphthyl isocyanate (1.692 g).

mp: 181.5°-183.5° C.

IR (Nujol): 3350, 3175, 3075, 1675 cm$^{-1}$

NMR (CDCl$_3$, δ): 2.40, (2H, m), 3.08 (2H, m), 3.48 (2H, m), 5.93 (2H, m), 6.28 (1H, s), 7.33-8.20 (7H, m), 8.87 (1H, s)

Analysis: Calcd. for C$_{16}$H$_{17}$N$_3$O

Calcd.: C 71.89, H 6.41, N 15.72;

Found: C 71.98, H 6.47, N 15.65.

EXAMPLE 16

N-[[(4-Fluorophenyl)carbamoyl]amino]morpholine (1.04 g) was obtained according to a similar manner to that of Example 7 from N-aminomorpholine (1.021 g) and 4-fluorophenyl isocyanate (1.645 g).

mp: 184°-185° C.

Mass: 239 (M+)

IR (Nujol): 3340, 3200, 3100, 1685 cm$^{-1}$

NMR (CD$_3$OD, δ):2.98 (4H, t, J=6 Hz), 3.80 (4H, t, J=6 Hz), 6.83-7.40 (4H, m),

Analysis: Calcd. for C$_{11}$H$_{14}$FN$_3$O

Calcd.: C 55.22, H 5.90, N 17.56;

Found: C 55.28, H 5.92, N 17.56.

EXAMPLE 17

1-[(4-Fluorophenyl)carbamoyl]-1,2,3,6-tetrahydropyridazine (2.43 g) was obtained according to a similar manner to that of Example 7 from 1,2,3,6-tetrahydropyridazine (1.777 g) and 4-fluorophenyl isocyanate (1.918 g).
mp: 100°–101° C.
IR (Nujol): 3330, 3250, 1670, 1650 cm$^{-1}$
NMR (CDCl$_3$, δ): 3.40 (3H, m), 4.07 (2H, m), 5.87 (2H, m), 6.78–7.53 (4H, m), 8.45 (1H, s),
Analysis: Calcd. for C$_{11}$H$_{12}$FN$_3$O
Calcd.: C 59.72, H 5.47, N 18.99;
Found: C 59.95, H 5.76, N 19.05.

EXAMPLE 18

1-[(4-Fluorophenyl)carbamoyl]-1,2-diazaspiro[2,5]-octane (1.03 g) was obtained according to a similar manner to that of Example 7 from 1,2-diazaspiro[2,5]-octane (1.122 g) and 4-fluorophenyl isocyanate (1.37 g).
mp: 140°–141° C.
Mass.: 249 (M$^+$)
IR (Nujol): 3270, 3200, 1675 cm$^{-1}$
NMR (CDCl$_3$, δ): 1.72 (10H, m), 2.42 (1H, s), 6.88–7.62 (4H, m), 8.05 (1H, s),

EXAMPLE 19

To a stirred solution of N-amino-4-phenyl-1,2,3,6-tetrahydropyridine hydrochloride (1.05 g) in a mixture of dioxane (10 ml) and water (5 ml) was added 1N sodium hydroxide solution (5 ml) under ice-bath cooling, and then a solution of 4-fluorophenyl isothiocyanate (1.15 g) in dioxane (5 ml) was added thereto. The mixture was stirred for 5 hours under ice-bath cooling. The reaction mixture was evaporated in vacuo and the residue was extracted several times with ethyl acetate. The combined extract was washed with water, dried over magnesium sulfate and evaporated in vacuo to give a crude product, which was recrystallized from ethyl acetate to give N-[[(4-fluorophenyl)thiocarbamoyl]amino]-4-phenyl-1,2,3,6-tetrahydropyridine (1.05 g).
mp: 192.5°–194.5° C.
IR (Nujol): 3300, 3125, 1540, 1510 cm$^{-1}$
NMR (CDCl$_3$, δ): 2.72 (2H, m), 3.17 (2H, m), 3.58 (2H, m), 5.97 (2H, m), 6.83–7.63 (4H, m), 7.27 (5H, s), 7.83 (1H, s), 9.12 (1H, s)
Analysis: Calcd. for C$_{18}$H$_{18}$FN$_3$S Calcd.: C 66.03, H 5.54, N 12.83; Found: C 66.79, H 5.63, N 12.65.

EXAMPLE 20

1,1-Diisopropyl-4-(4-fluorophenyl)thiosemicarbazide (0.42 g) was obtained according to a similar manner to that of Example 19 from 1,1-diisopropylhydrazine hydrochloride(4.575 g) and 4-fluorophenyl isothiocyanate (2.757 g).
mp: 127.5°–128.5° C.
Mass.: 269 (M$^+$)
IR (Nujol): 3290, 3150, 1525, 1510 cm$^{-1}$
NMR (CDCl$_3$, δ): 1.08 (6H,d, J=6 Hz), 1.13 (6H, d, J=6 Hz), 3.03–3.47 (2H, m), 6.87–7.63 (5H, m), 9.03 (1H, s)
Analysis: Calcd. for C$_{13}$H$_{20}$FN$_3$S Calcd.: C 57.96, H 7.48, N 15.60; Found: C 58.23, H 7.55, N 15.30.

EXAMPLE 21

N-Amino-1,2,3,6-tetrahydropyridine hydrochloride (3.768 g) was dissolved in a mixture of dioxane (60 ml) and water (30 ml). The solution was adjusted to pH 7 with 1N-aqueous sodium hydroxide, and to the resultant mixture was added a solution of 4-fluorophenyl isothiocyanate (3.984 g) in dioxane (20 ml). The mixture was kept to pH 7.5 and stirred for 6 hours at ambient temperature. After evaporation of organic solvent, the residue was extracted with ethyl acetate (300 ml). The extract was washed with water and dried over magnesium sulfate. The solvent was distilled off to give a residue (1.5 g), which was subjected to column chromatography on silica gel (37 g) eluting with chloroform. The fractions containing the desired compound were combined and concentrated under reduced pressure. The residue was recrystallized from ethyl acetate to give white needles of N-[[(4-fluorophenyl)thiocarbamoyl]amino]-1,2,3,6-tetrahydropyridine (0.779 g).
mp: 163°–164.5° C.
Mass: m/e=251 (M$^+$)
IR (Nujol): 3260, 2930, 1540, 1505, 1460 cm$^{-1}$
NMR (DMSO-d$_6$, δ): 2.88 (2H, m), 5.72 (2H, m), 7.00–7.73 (4H, m), 9.26 (1H, s), 9.60 (1H, s)
Analysis: Calcd. for C$_{12}$H$_{14}$N$_3$FS Calcd.: C 57.35, H 5.61, N 16.72; Found: C 57.17, H 5.92, N 16.53.

EXAMPLE 22

1,1-Diallyl-4-(4-fluorophenyl)thiosemicarbazide (0.57 g) was obtained according to a similar manner to that of Example 21 from 1,1-diallylhydrazine hydrochloride (1.48 g) and 4-fluorophenyl isothiocyanate (1.225 g).
mp: 73°–74 ° C.
Mass: m/e=265 (M$^+$)
IR (Nujol): 3240, 3150, 1546, 1500, 1460 cm$^{-1}$
NMR (CDCl$_3$, δ): 3.42 (4H, d, J=6 Hz), 5.1–6.3 (6H, m), 6.9–7.3 (5H, m), 9.03 (1H, br. s) Analysis: Calcd. for C$_{13}$H$_{16}$FN$_3$S
Calcd.: C 58.84, H 6.08, N 15.84;
Found: C 59.02, H 6.30, N 15.74.

EXAMPLE 23

1,1-Diphenyl-4-(4-fluorophenyl)thiosemicarbazide (0.88 g) was obtained according to a similar manner to that of Example 21 from 1,1-diphenylhydrazine (1.84 g) and 4-fluorophenyl isothiocyanate (1.84 g). mp: 199.5°–200.5° C.
Mass: m/e=337 (M$^+$)
IR (Nujol): 3340, 3000, 1586, 1524 cm$^{-1}$
NMR (DMSO-d$_6$, δ): 7.0–7.6 (14H, m), 10.22 (1H, s), 10.67 (1H, s)
Analysis: Calcd. for C$_{19}$H$_{16}$FN$_3$S
Calcd.: C 67.64, H 4.78, N 12.45;
Found C: 67.88, H 5.09, N 12.13.

EXAMPLE 24

The following compounds are obtained according to a similar manner to that of Example 1.
(1) N-[[(2-Fluorophenyl)carbamoyl]amino]-1,2,3,6-tetrahydropyridine.
mp: 119°–121° C.
IR (Nujol): 3360, 3200, 3100, 1690, 1620, 1600 cm$^{-1}$
(2) N-(Phenylcarbamoylamino)-1,2,3,6-tetrahydropyridine.
mp: 157°–159° C.
IR (Nujol): 3340, 3190, 3100, 1680 cm$^{-1}$
(3) 1-[(4-Fluorophenyl)carbamoyl]hexahadropyridazine.
mp: 78.5°–79.5° C.
IR (Nujol): 3375, 3250, 1685, 1600 cm$^{-1}$
(4) N-[[(4-Dimethylaminophenyl)carbamoyl]amino]-1,2,3,6-tetrahydropyridine.
mp: 179.5°–180° C.
IR (Nujol): 1680 cm$^{-1}$ (5) N-[[(4-Acetylphenyl)carbamoyl]amino]-1,2,3,6-tetrahydropyridine.
mp: 142.5°–143° C.
IR (Nujol): 1685, 1670 cm$^{-1}$
(6) N-[[(2,4-Difluorophenyl)carbamoyl]amino]-1,2,3,6-tetrahydropyridine.
mp: 136.5°–137° C.
IR (Nujol): 1695 cm$^{-1}$
(7) N-[[(4-Methoxycarbonylphenyl)carbamoyl]amino]-1,2,3,6-tetrahydropyridine.
mp: 182.5°–184° C.
IR (Nujol): 1715, 1680 cm$^{-1}$

EXAMPLE 25

A solution of 4-fluoro-N-phenoxycarbonylaniline (2.29 g), N-amino-1,2,3,6-tetrahydropyridine hydrochloride (1.346 g) and triethylamine (1.02 g) in chloroform (25 ml) was refluxed for 20 hours. After evaporation of chloroform, the residue was extracted with ethyl acetate (100 ml). The extract was washed with water, dried over magnesium sulfate and evaporated in vacuo. The residue was chromatographed on silica gel (20 g) using chloroform as an eluent to give N-[[(4-fluorophenyl)carbamoyl]amino]-1,2,3,6-tetrahydropyridine (1.05 g). mp: 156°–157° C.
Mass: m/e=235 (M$^+$)
IR (Nujol): 3380, 3190, 3100, 1680, 1660 cm$^{-1}$
NMR (CDCl$_3$, δ): 2.31 (2H, m), 2.92 (2H, t, J=7 Hz), 5.78 (2H, m), 6.87–7.48 (4H, m)
Analysis: Calcd. for C$_{12}$H$_{14}$FN$_3$O
Calcd.: C 61.26, H 6.00, N 17.84;
Found: C 61.37, H 6.06, N 18.04.

EXAMPLE 26

N-[[(2-Fluorophenyl)carbamoyl]amino]-1,2,3,6-tetrahydropyridine (0.56 g) was obtained according to a similar manner to that of Example 25 from N-amino-1,2,3,6-tetrahydropyridine hydrochloride (2.34 g) and 2-fluoro-N-phenoxycarbonylaniline (2.77 g).
mp: 119°–121° C.
IR (Nujol): 3360, 3200, 3100, 1690, 1620, 1600 cm$^{-1}$
NMR (CDCl$_3$, δ): 2.32 (2H, m), 2.98 (2H, m), 3.38 (2H, m), 5.71 (2H, m), 6.10 (1H, s), 6.94–7.20 (3H, m), 8.20–8.37 (1H, m), 8.53 (1H, s)
Analysis: Calcd. for C$_{12}$H$_{14}$FN$_3$O
Calcd.: C 61.26, H 6.00, N 17.86;
Found: C 61.87, H 6.09, N 17.95.

EXAMPLE 27

N-[[(4-Dimethylaminophenyl)carbamoyl]amino]-1,2,3,6-tetrahydropyridine (1.98 g) was obtained according to a similar manner to that of Example 25 from N-amino-1,2,3,6-tetrahydropyridine hydrochloride (2.02 g) and 4-(phenoxycarbonylamino)-N,N-dimethylaniline (2.56 g).
mp: 179.5°–180° C.
IR (Nujol): 1680 cm$^{-1}$
NMR (CDCl$_3$, δ): 2.26 (2H, m), 2.84 (6H, s), 2.70–3.13 (2H, m), 3.30 (2H, m), 5.66 (2H, m), 6.06 (1H, s)

EXAMPLE 28

N-[[(4-Acetylphenyl)carbamoyl]amino]-1,2,3,6-tetrahydropyridine (1.72 g) was obtained according to a similar manner to that of Example 25 from N-amino-1,2,3,6-tetrahydropyridine hydrochloride (1.94 g) and 4'-(phenoxycarbonylamino)acetophenone (3.06 g). mp: 142.5°–143° C.
IR (Nujol): 1685, 1670 cm$^{-1}$

EXAMPLE 29

N-[[(2,4-Difluorophenyl)carbamoyl]amino]-1,2,3,6-tetrahydropyridine (1.14 g) was obtained according to a similar manner to that of Example 25 from N-amino-1,2,3,6-tetrahydropyridine hydrochloride (2.22 g) and 2,4-difluoro-N-phenoxycarbonylaniline (2.74 g). mp: 136.5°–137° C.
IR (Nujol): 1695 cm$^{-1}$
NMR (CDCl$_3$, δ): 2.06–2.50 (2H, m), 2.73–3.09 (2H, m), 3.15–3.64 (2H, m), 5.56–5.87 (2H, m), 5.90–6.23 (1H, m), 6.59–7.13 (2H, m), 7.88–8.48 (2H, m)

EXAMPLE 30

The following compounds are obtained according to a similar manner to that of Example 25.
(1) N-[[(4-Fluorophenyl)carbamoyl]amino]-4-phenyl-1,2,3,6-tetrahydropyridine.
mp: 200.5°–212° C.
IR (Nujol): 3340, 3160, 3070, 1670, 1540 cm$^{-1}$
(2) 1,1-Diisopropyl-4-(4-fluorophenyl)semicarbazide.
mp: 126.5°–128° C.
IR (Nujol): 3320, 3080, 1680, 1500–1540 cm$^{-1}$
(3) 1-Benzyl-4-(4-fluorophenyl)semicarbazide.
mp: 102° C.
IR (Nujol): 3260, 1640 cm$^{-1}$
(4) 1,1-Diallyl-4-(4-fluorophenyl)semicarbazide.
IR (Film): 3350, 3225, 3080, 1685 cm$^{-1}$
(5) 1,1-Diphenyl-4-(4-fluorophenyl)semicarbazide.
mp: 214°–214.5° C.
IR (Nujol): 3280, 1640, 1600, 1585 cm$^{-1}$
(6) N-[[(3-Fluorophenyl)carbamoyl]amino]-1,2,3,6-tetrahydropyridine.
mp: 136.5°–138.5° C.
IR (Nujol): 3280, 3200, 3100, 1685 cm$^{-1}$
(7) N-[[(4-Chlorophenyl)carbamoyl]amino]-1,2,3,6-tetrahydropyridine.
mp: 165.5°–167.5° C.
IR (Nujol): 3330, 3170, 3100, 1685 cm$^{-1}$
(8) N-[[(3-Chlorophenyl)carbamoyl]amino]-1,2,3,6-tetrahydropyridine.
mp: 145.5°–147° C.
IR (Nujol): 3340, 3190, 3090, 1680 cm$^{-1}$
(9) N-[[(2-Methoxy-5-chlorophenyl)carbamoyl]amino]-1,2,3,6-tetrahydropyridine.
mp: 153.5°–154.5° C.
IR (Nujol): 3375, 3300, 3200, 3100, 1680 cm$^{-1}$
(10) N-[[(4-Methoxyphenyl)carbamoyl]amino]-1,2,3,6-tetrahydropyridine.
mp: 146°–147° C.
IR (Nujol): 3300, 3200, 3180, 3100, 1680 cm$^{-1}$
(11) N-[[(2-Methoxyphenyl)carbamoyl]amino]-1,2,3,6-tetrahydropyridine.
mp: 137°–139° C.
IR (Nujol): 3330, 3200, 3100, 1680 cm$^{-1}$
(12) N-[(p-Tolylcarbamoyl)amino]-1,2,3,6-tetrahydropyridine.
mp: 179°–180° C.
IR (Nujol): 3350, 3170, 3050, 1675 cm$^{-1}$
(13) N-[[(4-Trifluoromethylphenyl)carbamoyl]amino]-1,2,3,6-tetrahydropyridine.
mp: 159.5°–161° C.
IR (Nujol): 3340, 3200, 3100, 1690 cm$^{-1}$
(14) N-[(1-Naphthylcarbamoyl)amino]-1,2,3,6-tetrahydropyridine.
mp: 181.5°–183.5° C.
IR (Nujol): 3350, 3175, 3075, 1675 cm$^{-1}$
(15) N-[[(4-Fluorophenyl)carbamoyl]amino]morpholine.
mp: 184°–185° C.

IR (Nujol): 3340, 3200, 3100, 1685 cm$^{-1}$

(16) 1-[(4-Fluorophenyl)carbamoyl]-1,2,3,6-tetrahydropyridazine.

mp: 100°–101° C.

IR (Nujol): 3330, 3250, 1670, 1650 cm$^{-1}$

(17) 1-[(4-Fluorophenyl)carbamoyl]-1,2-diazaspiro[2,5]octane.

mp: 140°–141° C.

IR (Nujol): 3270, 3200, 1675 cm$^{-1}$

(18) N-(Phenylcarbamoylamino)-1,2,3,6-tetrahydropyridine.

mp: 157°–159° C.

IR (Nujol): 3340, 3190, 3100, 1680 cm$^{-1}$

(19) 1-[(4-Fluorophenyl)carbamoyl]hexahydropyridazine.

mp: 78.5°–79.5° C.

IR (Nujol): 3375, 3250, 1685, 1600 cm$^{-1}$

(20) N-[(N-Methyl-N-phenylcarbamoyl)amino]-1,2,3,6-tetrahydropyridine.

mp: 99°–99.5° C.

IR (Nujol): 3250, 2950, 2870, 1645 cm$^{-1}$

(21) N-[[(4-Hydroxyphenyl)carbamoyl]amino]-1,2,3,6-tetrahydropyridine.

mp: 185.5°–187° C.

IR (Nujol): 3190, 1660 cm$^{-1}$

(22) N-[[(4-Methoxycarbonylphenyl)carbamoyl]amino]-1,2,3,6-tetrahydropyridine.

mp: 182.5°–183° C.

IR (Nujol): 1715, 1680 cm$^{-1}$

(23) N-[[(4-Carboxyphenyl)carbamoyl]amino]-1,2,3,6-tetrahydropyridine.

mp: >240° C.

IR (Nujol): 1700 cm$^{-1}$

(24) N-[[(4-Fluorophenyl)thiocarbamoyl]amino]-1,2,3,6-tetrahydropyridine.

mp: 163°–164.5° C.

IR (Nujol): 3260, 2930, 1540, 1505, 1460 cm$^{-1}$

(25) 1,1-Diallyl-4-(4-fluorophenyl)thiosemicarbazide.

mp: 73°–74° C.

IR (Nujol): 3240, 3150, 1546, 1500, 1460 cm$^{-1}$

(26) 1,1-Diphenyl-4-(4-fluorophenyl)thiosemicarbazide.

mp: 199.5°–200.5° C.

IR (Nujol): 3340, 3000, 1586, 1524 cm$^{-1}$

(27) N-[[(4-Fluorophenyl)thiocarbamoyl]amino]-4-phenyl-1,2,3,6-tetrahydropyridine.

mp: 192.5°–194.5° C.

IR (Nujol): 3300, 3125, 1540, 1510 cm$^{-1}$

(28) 1,1-Diisopropyl-4-(4-fluorophenyl)-thiosemicarbazide.

mp: 127.5°–128.5° C.

IR (Nujol): 3290, 3150, 1525, 1510 cm$^{-1}$

EXAMPLE 31

N-[[(4-Fluorophenyl)carbamoyl]amino]-1,2,3,6-tetrahydropyridine (0.70 g) was obtained according to a similar manner to that of Example 25 from N-(phenoxycarbonylamino)-1,2,3,6-tetrahydropyridine (1.09 g) and 4-fluoroaniline (0.555 g).

mp: 156°–157° C.

Mass: m/e=235 (M+)

IR (Nujol): 3380, 3190, 3100, 1680, 1660 cm$^{-1}$

NMR (CDCl$_3$, δ): 2.31 (2H, m), 2.92 (2H, t, J=7 Hz), 5.78 (2H, m), 6.87–7.48 (4H, m)

Analysis: Calcd. for C$_{12}$H$_{14}$FN$_3$O

Calcd.: C 61.26, H 6.00, N 17.84

Found: C 61.37, H 6.06, N 18.04

EXAMPLE 32

N-[(N-Methyl-N-phenylcarbamoyl)amino]-1,2,3,6-tetrahydropyridine (1.24 g) was obtained according to a similar manner to that of Example 25 from N-phenoxycarbonylamino-1,2,3,6-tetrahydropyridine (2.18 g) and N-methylaniline (2.19 g). mp: 99°–99.5° C.

IR (Nujol): 3250, 2950, 2870, 1645 cm$^{-1}$

NMR (CDCl$_3$, δ): 2.13 (2H, m), 2.86 (2H, t, J=6 Hz), 3.16 (3H, s), 3.13–3.46 (2H, m), 5.23–5.76 (2H, m), 7.02–7.53 (5H, m)

EXAMPLE 33

N-[[(4-Hydroxyphenyl)carbamoyl]amino]-1,2,3,6-tetrahydropyridine (1.04 g) was obtained according to a similar manner to that of Example 25 from N-phenoxycarbonylamino-1,2,3,6-tetrahydropyridine (1.53 g) and 4-hydroxyaniline (1.09 g). mp : 185.5°–187° C.

IR (Nujol): 3190, 1660 cm$^{-1}$

NMR (CD$_3$OD, δ): 2.10–2.58 (2H, m), 2.93 (2H, t, J=5.5 Hz), 3.20–3.52 (2H, m), 5.59–5.86 (2H, m), 6.70 (2H, d, J=8 Hz), 7.20 (2H, d, J=8 Hz)

EXAMPLE 34

N-[[(4-Methoxycarbonylphenyl)carbamoyl]amino]-1,2,3,6-tetrahydropyridine (1.25 g) was obtained according to a similar manner to that of Example 25 from N-phenoxycarbonylamino-1,2,3,6-tetrahydropyridine (1.53 g) and methyl 4-aminobenzoate (1.51 g).

mp: 182.5°–183° C.

IR (Nujol): 1715, 1680 cm$^{-1}$

NMR (CDCl$_3$, δ): 2.16–2.63 (2H, m), 2.76–3.23 (2H, m), 3.26–3.74 (2H, m), 3.87 (3H, s), 5.53–5.98 (2H, m), 6.04 (1H, s), 7.58 (2H, d, J=6 Hz), 8.02 (2H, d, J=6 Hz), 8.44 (1H, s)

EXAMPLE 35

The following compounds are obtained according to a similar manner to that of Example 25.

(1) N-[[(4-Fluorophenyl)carbamoyl]amino]-4-phenyl1,2,3,6-tetrahydropyridine.

mp: 200.5°–212° C.

IR (Nujol): 3340, 3160, 3070, 1670, 1540 cm$^{-1}$ (2) 1,1-Diisopropyl-4-(4-fluorophenyl)semicarbazide.

mp: 126.5°–128° C.

IR (Nujol): 3320, 3080, 1680, 1500–1540 cm$^{-1}$ (3) 1-Benzyl-4-(4-fluorophenyl)semicarbazide.

mp: 102° C.

IR (Nujol): 3260, 1640 cm$^{-1}$ (4) 1,1-Dially-4-(4-fluorophenyl)semicarbazide.

IR (Film): 3350, 3225, 3080, 1685 cm$^{-1}$ (5) 1,1-Diphenyl-4-(4-fluorophenyl)semicarbazide.

mp: 214°–214.5° C.

IR (Nujol): 3280, 1640, 1600, 1585 cm$^{-1}$ (6) N-[[(3-Fluorophenyl)carbamoyl]amino]-1,2,3,6-tetrahydropyridine.

mp: 136.5°–138.5° C.

IR (Nujol): 3280, 3200, 3100, 1685 cm$^{-1}$ (7) N-[[(4-Chlorophenyl)carbamoyl]amino]-1,2,3,6-tetrahydropyridine.

mp: 165.5°–167.5° C.

IR (Nujol): 3330, 3170, 3100, 1685 cm$^{-1}$ (8) N-[[(3-Chlorophenyl)carbamoyl]amino]-1,2,3,6-tetrahydropyridine.

mp: 145.5°–147° C.

IR (Nujol): 3340, 3190, 3090, 1680 cm$^{-1}$ (9) N-[[(2-Methoxy-5-chlorophenyl)carbamoyl]amino]-1,2,3,6-tetrahydropyridine.

mp: 153.5°–154.5° C.

IR (Nujol): 3375, 3300, 3200, 3100, 1680 cm$^{-1}$

(10) N-[[(4-Methoxyphenyl)carbamoyl]amino]-1,2,3,6-tetrahydropyridine.
mp: 146°–147° C.
IR (Nujol): 3300, 3200, 3180, 3100, 1680 cm$^{-1}$

(11) N-[[(2-Methoxyphenyl)carbamoyl]amino]-1,2,3,6-tetrahydropyridine.
mp: 137°–139° C.
IR (Nujol): 3330, 3200, 3100, 1680 cm$^{-1}$

(12) N-[(p-Tolylcarbamoyl)amino]-1,2,3,6-tetrahydropyridine.
mp: 179°–180° C.
IR (Nujol): 3350, 3170, 3050, 1675 cm$^{-1}$

(13) N-[[(4-Trifluoromethylphenyl)carbamoyl]amino]-1,2,3,6-tetrahydropyridine.
mp: 159.5°–161° C.
IR (Nujol): 3340, 3200, 3100, 1690 cm$^{-1}$

(14) N-[(1-Naphthylcarbamoyl)amino]-1,2,3,6-tetrahydropyridine.
mp: 181.5°–183.5° C.
IR (Nujol): 3350, 3175, 3075, 1675 cm$^{-1}$

(15) N-[[(4-Fluorophenyl)carbamoyl]amino]morpholine.
mp: 184°–185° C.
IR (Nujol): 3340, 3200, 3100, 1685 cm$^{-1}$

(16) 1-[(4-Fluorophenyl)carbamoyl]-1,2,3,6-tetrahydropyridazine.
mp: 100°–101° C.
IR (Nujol): 3330, 3250, 1670, 1650 cm$^{-1}$

(17) 1-[(4-Fluorophenyl)carbamoyl]-1,2-diazaspiro[2,5]octane.
mp: 140°–141° C.
IR (Nujol): 3270, 3200, 1675 cm$^{-1}$

(18) N-(Phenylcarbamoylamino)-1,2,3,6-tetrahydropyridine.
mp: 157°–159° C.
IR (Nujol): 3340, 3190, 3100, 1680 cm$^{-1}$

(19) 1-[(4-Fluorophenyl)carbamoyl]hexahydropyridazine.
mp: 78.5°–79.5° C.
IR (Nujol): 3375, 3250, 1685, 1600 cm$^{-1}$

(20) N-[[(2-Fluorophenyl)carbamoyl]amino]-1,2,3,6-tetrahydropyridine.
mp: 119°–121° C.
IR (Nujol): 3360, 3200, 3100, 1690, 1620, 1600 cm$^{-1}$

(21) N-[[(4-Dimethylaminophenyl)carbamoyl]amino]-1,2,3,6-tetrahydropyridine.
mp: 179.5°–180° C.
IR (Nujol): 1680 cm$^{-1}$

(22) N-[[(4-Acetylphenyl)carbamoyl]amino]-1,2,3,6-tetrahydropyridine.
mp: 142.5°–143° C.
IR (Nujol): 1685, 1670 cm$^{-1}$ (23) N-[[(2,4-Difluorophenyl)carbamoyl]amino]-1,2,3,6-tetrahydropyridine.
mp: 136.5°–137° C.
IR (Nujol): 1695 cm$^{-1}$

(24) N-[[(4-Carboxyphenyl)carbamoyl]amino]-1,2,3,6-tetrahydropyridine.
mp: >240° C.
IR (Nujol): 1700 cm$^{-1}$

(25) N-[[(4-Fluorophenyl)thiocarbamoyl]amino]-1,2,3,6-tetrahydropyridine.
mp: 163°–164.5° C.
IR (Nujol): 3260, 2930, 1540, 1505, 1460 cm$^{-1}$

(26) 1,1-Diallyl-4-(4-fluorophenyl)thiosemicarbazide.
mp: 73°–74° C.
IR (Nujol): 3240, 3150, 1546, 1500, 1460 cm$^{-1}$

(27) 1,1-Diphenyl-4-(4-fluorophenyl)thiosemicarbazide.
mp: 199.5°–200.5° C.
IR (Nujol): 3340, 3000, 1586, 1524 cm$^{-1}$

(28) N-[[(4-Fluorophenyl)thiocarbamoyl]amino]-4-phenyl-1,2,3,6-tetrahydropyridine.
mp: 192.5°–194.5° C.
IR (Nujol): 3300, 3125, 1540, 1510 cm$^{-1}$

(29) 1,1-Diisopropyl-4-(4-fluorophenyl)-thiosemicarbazide.
mp: 127.5°–128.5° C.
IR (Nujol): 3290, 3150, 1525, 1510 cm$^{-1}$

EXAMPLE 36

To a solution of N-(phenylcarbamoylimino)-pyridinium ylide (0.64 g) in a mixture of ethanol (30 ml) and water (10 ml) was added sodium borohydride (0.20 g) at ambient temperature. After being stirred for 4 hours, the reaction mixture was acidified with 1N hydrochloric acid, concentrated to a volume of ca. 15 ml. The crystalline precipitate was collected, washed with water and dried in vacuo. The crude product was dissolved in ethyl acetate and extracted with 10% hydrochloric acid (20 ml). The extract was adjusted to pH 3 with aqueous sodium bicarbonate and extracted with ethyl acetate (30 ml). The organic layer was washed with aqueous sodium bicarbonate (10 ml), dried over magnesium sulfate and evaporated to give N-(phenylcarbamoylamino)-1,2,3,6-tetrahydropyridine (0.28 g), which was recrystallized from ethyl acetate to afford colorless needles (0.15 g). mp: 157°–159° C.
IR (Nujol): 3340, 3190, 3100, 1680 cm$^{-1}$
NMR (CD$_3$OD, δ): 2.36 (2H, m), 2.96 (2H, t, J=5.5 Hz), 5.73 (2H, m), 7.0–7.6 (5H, m)

EXAMPLE 37

A suspension of N-[[(4-fluorophenyl)carbamoyl]imino]pyridinium ylide (1.04 g) and sodium borohydride (2.55 g) in ethanol (100 ml) was stirred at ambient temperature for 16 hours. Excess of sodium borohydride was decomposed with water, and the resulting mixture was evaporated. The residue was extracted with chloroform (20 ml×3). The combined organic extract was washed with water, dried over magnesium sulfate and evaporated to give crystals. Recrystallization from diisopropyl ether gave N-[[(4-fluorophenyl)carbamoyl]amino]-1,2,3,6-tetrahydropyridine (0.60 g).
mp: 156°–157° C.
IR (Nujol): 3340, 3200, 3100, 1680, 1605 cm$^{-1}$
NMR (CDCl$_3$, δ): 2.31 (2H, m), 2.92 (2H, t, J=7 Hz), 5.78 (2H, m), 6.87–7.48 (4H, m)

EXAMPLE 38

The following compounds are obtained according to a similar manner to that of Example 36.

(1) N-[[(4-Fluorophenyl)carbamoyl]amino]-4-phenyl-1,2,3,6-tetrahydropyridine.
mp: 200.5°–212° C.
IR (Nujol): 3340, 3160, 3070, 1670, 1540 cm$^{-1}$ (2) N-[[(3-Fluorophenyl)carbamoyl]amino]-1,2,3,6-tetrahydropyridine.
mp: 136.5°–138.5° C.
IR (Nujol): 3280, 3200, 3100, 1685 cm$^{-1}$ (3) N-[[(4-Chlorophenyl)carbamoyl]amino]-1,2,3,6-tetrahydropyridine.
mp: 165.5°–167.5° C.
IR (Nujol): 3330, 3170, 3100, 1685 cm$^{-1}$ (4) N-[[(3-Chlorophenyl)carbamoyl]amino]-1,2,3,6-tetrahydropyridine.
mp: 145.5°–147° C.
IR (Nujol): 3340, 3190, 3090, 1680 cm$^{-1}$ (5) N-[[(2-Methoxy-5-chlorophenyl)carbamoyl]amino]-1,2,3,6-tetrahydropyridine.

mp: 153.5°–154.5° C.
IR (Nujol): 3375, 3300, 3200, 3100, 1680 cm$^{-1}$ (6) N-[[(4-Methoxyphenyl)carbamoyl]amino]-1,2,3,6-tetrahydropyridine.
mp: 146°–147° C.
IR (Nujol): 3300, 3200, 3180, 3100, 1680 cm$^{-1}$ (7) N-[[(2-Methoxyphenyl)carbamoyl]amino]-1,2,3,6-tetrahydropyridine.
mp: 137°–139° C.
IR (Nujol): 3330, 3200, 3100, 1680 cm$^{-1}$ (8) N-[(p-Tolylcarbamoyl)amino]-1,2,3,6-tetrahydropyridine.
mp: 179°–180° C.
IR (Nujol): 3350, 3170, 3050, 1675 cm$^{-1}$ (9) N-[[(4-Trifluoromethylphenyl)carbamoyl]amino]-1,2,3,6-tetrahydropyridine.
mp: 159.5°–161° C.
IR (Nujol): 3340, 3200, 3100, 1690 cm$^{-1}$

(10) N-[(1-Naphthylcarbamoyl)amino]-1,2,3,6-tetrahydropyridine.
mp: 181.5°–183.5° C.
IR (Nujol): 3350, 3175, 3075, 1675 cm$^{-1}$

(11) N-[[(2-Fluorophenyl)carbamoyl]amino]-1,2,3,6-tetrahydropyridine.
mp: 119°–121° C.
IR (Nujol): 3360, 3200, 3100, 1690, 1620, 1600 cm$^{-1}$

(12) N-[[(4-Dimethylaminophenyl)carbamoyl]amino]-1,2,3,6-tetrahydropyridine.
mp: 179.5°–180° C.
IR (Nujol): 1680 cm$^{-1}$

(13) N-[[(2,4-Difluorophenyl)carbamoyl]amino]-1,2,3,6-tetrahydropyridine.
mp: 136.5°–137° C.
IR (Nujol): 1695 cm$^{-1}$

(14) N-[(N-Methyl-N-phenylcarbamoyl)amino]-1,2,3,6-tetrahydropyridine.
mp: 99°–99.5° C.
IR (Nujol): 3250, 2950, 2870, 1645 cm$^{-1}$

(15) N-[[(4-Hydroxyphenyl)carbamoyl]amino]-1,2,3,6-tetrahydropyridine.
mp: 185.5°–187° C.
IR (Nujol): 3190, 1660 cm$^{-1}$

(16) N-[[(4-Methoxycarbonylphenyl)carbamoyl]amino]-1,2,3,6-tetrahydropyridine.
mp: 182.5°–183° C.
IR (Nujol): 1715, 1680 cm$^{-1}$

(17) N-[[(4-Carboxyphenyl)carbamoyl]amino]-1,2,3,6-tetrahydropyridine.
mp: >240° C.
IR (Nujol): 1700 cm$^{-1}$

(18) N-[[(4-Fluorophenyl)thiocarbamoyl]amino]-1,2,3,6-tetrahydropyridine.
mp: 163°–164.5° C.
IR (Nujol): 3260, 2930, 1540, 1505, 1460 cm$^{-1}$

(19) N-[[(4-Fluorophenyl)thiocarbamoyl]amino]-4-phenyl-1,2,3,6-tetrahydropyridine.
mp: 192.5°–194.5° C.
IR (Nujol): 3300, 3125, 1540, 1510 cm$^{-1}$

EXAMPLE 39

A solution of 1-[(4-fluorophenyl)carbamoyl]-1,2,3,6-tetrahydropyridazine (1.327 g) in acetic acid (40 ml) was hydrogenated under an atmospheric pressure of hydrogen over 10% palladium charcoal (400 mg). After removal of the catalyst, the solvent was evaporated under reduced pressure to give an oil (0.8 g), which was subjected to column chromatography on silica gel (16 g) eluting with chloroform. The fractions containing the desired compound were combined and concentrated under reduced pressure. The residue was recrystallized from diethyl ether to give white needles of 1-[(4-fluorophenyl)carbamoyl]hexahydropyridazine (0.3 g).
mp: 78.5°–79.5° C.
IR (Nujol): 3375, 3250, 1685, 1600 cm$^{-1}$
NMR (CD$_3$OD, δ): 1.80–2.00 (4H, m), 2.30 (2H, m), 3.73 (2H, t, J=6 Hz), 6.89–7.50 (4H, m)

EXAMPLE 40

1-[(4-Fluorophenyl)carbamoyl]-1,2,3,6-tetrahydropyridazine is obtained according to a similar manner to that of Example 39.
mp: 100°–101° C.
IR (Nujol): 3330, 3250, 1670, 1650 cm$^{-1}$

EXAMPLE 41

To a solution of N-[[(4-methoxycarbonylphenyl)-carbamoyl]amino]-1,2,3,6-tetrahydropyridine (1.21 g) in a mixture of methanol (30 ml) and chloroform (30 ml) was added. 1N sodium hydroxide (10 ml) and the mixture was stirred at ambient temperature for 18 hours. After evaporation of the solvent, the residue was extracted with chloroform (20 ml×3). The extract was washed with water, dried over magnesium sulfate and concentrated in vacuo. The residue was purified by column chromatography on silica gel (40 g) eluting with chloroform, to give N-[[(4-carboxyphenyl)-carbamoyl]amino]-1,2,3,6-tetrahydropyridine (0.65 g).
mp: >240° C.
IR (Nujol): 1700 cm$^{-1}$
NMR (D$_2$O+NaOD, δ): 2.12–2.49 (2H, m), 2.94 (2H, t, J=5 Hz), 3.16–3.44 (2H, m), 5.68–6.01 (2H, m), 7.41 (2H, d, J=8 Hz), 7.87 (2H, d, J=8 Hz)

What we claimed is:

1. A compound of the formula:

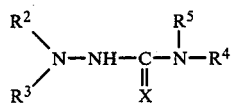

wherein
R$^2$ and R$^3$ are taken together with the adjacent nitrogen atom to form tetrahydropyridyl optionally substituted with phenyl,
R$^4$ is phenyl or naphthyl optionally substituted with lower alkyl, halogen, lower alkylamino, halo (lower) alkyl, hydroxy, lower alkanoyl, carboxy or esterified carboxy,
R$^5$ is hydrogen or lower alkyl, and
X is O or S,
and pharmaceutically acceptable salts thereof.

2. A compound of claim 1, wherein X is O.

3. A compound of claim 2, wherein R$^4$ is phenyl optionally having substituent(s) selected from halogen and lower alkylamino.

4. A compound of claim 3, which is N-(phenylcarbamoylamino)-1,2,3,6-tetrahydropyridine.

5. A compound of claim 3, which is N-[[(2-fluorophenyl)carbamoyl]amino]-1,2,3,6-tetrahydropyridine.

6. A compound of claim 3, which is N-[[(3-fluorophenyl)carbamoyl]amino]-1,2,3,6-tetrahydropyridine.

7. A compound of claim 3, which is N-[[(4-fluorophenyl)carbamoyl]amino]-1,2,3,6-tetrahydropyridine.

8. An antiinflammatory and analgesic, pharmaceutical composition comprising an effective antiinflammatory or analgesic amount of a compound of claim 1 in association with a pharmaceutically acceptable, substantially nontoxic carrier or excipient.

9. A method for treatment of inflammation which comprises administering an effective antiinflammatory amount of a compound of claim 1 to human beings or animals.

10. A method for treatment of pain which comprises administering an effective analgesic amount of a compound of claim 1 to human beings or animals.

* * * * *